United States Patent
Ach

(10) Patent No.: US 6,723,509 B2
(45) Date of Patent: Apr. 20, 2004

(54) METHOD FOR 3' END-LABELING RIBONUCLEIC ACIDS

(75) Inventor: Robert A. Ach, San Francisco, CA (US)

(73) Assignee: Agilent Technolgies, Inc., Palo Alto, CA (US)

( * ) Notice: Subject to any disclaimer, the term of this patent is extended or adjusted under 35 U.S.C. 154(b) by 63 days.

(21) Appl. No.: 09/802,358

(22) Filed: Mar. 9, 2001

(65) Prior Publication Data

US 2001/0009762 A1 Jul. 26, 2001

Related U.S. Application Data

(62) Division of application No. 09/359,564, filed on Jul. 22, 1999, now Pat. No. 6,201,112.

(51) Int. Cl.$^7$ .......................... C12Q 1/68; C12N 15/00; C12N 15/63; C12N 1/20; C07H 21/04
(52) U.S. Cl. .................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .................... 435/6, 91.1, 91.2; 536/24.3; 935/6; 436/518

(56) References Cited

U.S. PATENT DOCUMENTS

| | | | |
|---|---|---|---|
| 5,231,191 A | 7/1993 | Woo et al. | 549/220 |
| 5,268,486 A | 12/1993 | Waggoner et al. | 548/427 |
| 5,380,833 A * | 1/1995 | Urdea | 536/22.1 |
| 5,525,497 A | 6/1996 | Keller et al. | 435/194 |
| 5,573,913 A | 11/1996 | Rosemeyer et al. | 435/6 |
| 5,714,386 A | 2/1998 | Roederer et al. | 436/546 |
| 6,479,303 B1 * | 11/2002 | Waggoner | 436/546 |

OTHER PUBLICATIONS

Martin George, Tailing and 3'-end labeling of RNA with yeast poly(A) polymerase and various nucleotides, RNA (1998), Cambridge University Press, pp. 226–230.*
Stratagene Catalog, 1988, The Gene Characterization Kits.*
Cao, Gong–Jie et al., Identification of the coding region for a second poly(A) polymerase in *Escherichia coli*; Proc. Natl. Acad. Sci. USA, vol 93, pp 11580–11585, Oct. 1996.*
Life Ttechnologies catalog, "PolyA Polymerase", p. 13–11, 1995–1996.*
Mathews et al., "Analytical strategies for the use of DNA probes", Analytical Biochemistry, vol. 169, pp. 1–25, 1988.*
Alberts et al., "Molecular Biology of the Cell: Third Edition", Garland Publishing, Inc., New York, 1994.
Linger & Keller, "3' End labeling of RNA with Recombinant Yeast poly(A) Polymerase", Nucleic Acids Research, vol. 21, pp. 2917–2920, 1993.
Martin & Keller, "Tailing and 3'-end Labeling of RNA with Yeast Poly(A) Polymerase and Various Nucleiotides", RNA, vol. 4, pp. 226–230, 1996.
Weissman, S.M., Methods of DNA & RNA Sequencing (Praeger, 1983), pp.261–304.
Richardson & Gumport, "Blotin and Fluorescent Labeling of RNA Using T4 RNA Ligase", Nucleic Acids Research, vol. 11, pp. 6167–6184, 1983.
Rosemeyer et al., "Nonradioactive 3'End–Labeling of RNA Molecules of Different Lengths by Terminal Deoxynucleotidyltransferase", Anal. Biochem., vol. 224, pp. 446–449, 1995.
Sippel, "Purification and Characterization of Adenosine Triphosphate; Ribonucleic Acid Adenyltransferase from *Escherichia Coli*", Eur. J. Biochem., vol. 37, pp. 31–40, 1973.
Winter & Brownlee, "3' End Labelling of RNA with 32P Suitable for Rapid Gel Sequencing", Nucleic Acids Research, vol. 5, pp. 3129–3139, 1978.

* cited by examiner

Primary Examiner—Jeffrey Fredman
Assistant Examiner—Arun Chakrabarti

(57) ABSTRACT

Methods of end-labeling ribonucleic acids with non-radioactively labeled ribonucleotides, and particularly fluorescently labeled ribonucleotides, are provided. In the subject methods, a ribonucleic acid is contacted with a non-radioactively labeled ribonucleotide in the presence of a prokaryotic, usually bacterial, poly(A) polymerase under conditions sufficient for covalent bonding of the labeled ribonucleotide to the 3' end of the ribonucleic acid to occur. Also provided are kits for practicing the subject method. The subject methods and kits find use in a variety of applications where labeling of the 3' end of a ribonucleic acid with a non-radioactive label, particularly a fluorescent label, is desired.

14 Claims, No Drawings ent labels. In the subject ribonucleic acid end-labeling methods, ribonucleic acid is contacted with non-radioactively labeled ribonucleotides, e.g. fluorescently labeled ribonucleotide, under conditions sufficient for covalent attachment of the labeled ribonucleotides to the 3' end of the ribonucleic acid to occur. The subject methods and kits find use in a variety of applications in which the end-labeling of ribonucleic acid with a non-radioactive label is desired.

METHOD FOR 3' END-LABELING RIBONUCLEIC ACIDS

CROSS-REFERENCE TO RELATED APPLICATIONS

This application is a divisional of U.S. patent application Ser. No. 09/359,564, filed Jul. 22, 1999 now U.S. Pat. No. 6,201,112.

TECHNICAL FIELD

The field of this invention is nucleic acids, particularly nucleic acid labeling techniques, and more particularly ribonucleic acid labeling techniques.

BACKGROUND OF THE INVENTION

The end-labeling of ribonucleic acids is fundamental to a variety of molecular biology applications. Applications in which RNA is end-labeled include: hybridization assays, in which the probe employed is an end-labeled ribonucleic acid of the subject invention, e.g. Southern analyses, northern analyses, DNA library screens, in situ hybridization experiments, e.g. chromosome squashes, tissue sections, etc.; sequencing applications, e.g. RNA direct chemical sequencing methods; hybridizations of labeled RNAs to chips/arrays; and the like.

A number of different protocols have been developed for 3'-end labeling RNA. In a first method that has been reported in the literature, bacteriophage T4 RNA ligase is used to attach radioactively labeled ribonucleotides to the 3' end of RNA molecules. Such ligase reactions typically require long incubation times to achieve sufficient labeling, e.g. 12 hours. In another method, terminal deoxynucleotidyl transferase (TdT) is employed to attach labeled deoxyribonucleotides to the 3' ends of RNAs. Disadvantages of this method include the fact that TdT cannot label with ribonucleotides (i.e. it cannot use ribonucleotides as donors) and that TdT uses both DNA and RNA as a substrate. Finally, poly(A) polymerase has been employed to label RNAs with radioactively labeled ribonucleotides. Disadvantages with this protocol include the use of radioactively labeled materials.

As such, despite the number of different protocols that have been developed for the 3' end-labeling of ribonucleic acids, there continues to be interest in the development of new methods for end-labeling ribonucleic acids. Of particular interest would be the development of a method of end-labeling ribonucleic acids which was able to rapidly and efficiently label a ribonucleic acid with non-radioactively labeled ribonucleotides, particularly fluorescently labeled ribonucleotides.

RELEVANT LITERATURE

U.S. Patents of interest include: U.S. Pat. Nos. 5,525,497 and 5,573,913. Also of interest are: Linger et al., Nuc. Acids Res. (1993) 21:2917–2920; Martin & Keller, RNA (1998) 4:226–230; Wiessman, S. M., METHODS OF DNA & RNA SEQUENCING, (Praeger, 1983) pp261–304; Richardson & Gumport, Nuc. Acids Res. (1983) 11:6167–6184; Rosemeyer et al., Anal. Biochem. (1995) 224: 446–449; Sippel, J. Biochem. (1973) 37:31–40; and Winter & Brownlee, Nuc. Acids Res. (1978) 5:3129–3139.

SUMMARY OF THE INVENTION

Methods and kits are provided for end-labeling ribonucleic acids with non-radioactive labels, particularly fluo-

DEFINITIONS

The term "nucleic acid" as used herein means a polymer made up of nucleotides, e.g. deoxyribonucleotides or ribonucleotides.

The terms "ribonucleic acid" and "RNA" as used herein means a polymer that includes at least one ribonucleotide at its 3' end, e.g. a polymer made up completely of ribonucleotides.

The terms "deoxyribonucleic acid" and "DNA" as used herein mean a polymer made up of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

DESCRIPTION OF THE SPECIFIC EMBODIMENTS

Methods are provided for end-labeling ribonucleic acids with non-radioactive labels. In the subject methods, ribonucleic acid is contacted with non-radioactively labeled ribonucleotides, e.g. fluorescently labeled ribonucleotide, in the presence of a prokaryotic poly(A) polymerase under conditions sufficient for covalent attachment of one or more of the labeled ribonucleotides to the 3' end of the ribonucleic acid to occur. Also provided are kits for practicing the subject methods. In further describing the subject invention, the subject methods will be discussed first in greater detail followed by a description of the kits for practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Methods

As summarized above, the subject invention is directed to methods of end-labeling ribonucleic acids with non-radioactive labels. In the broadest sense, ribonucleic acids that may be end-labeled according to the methods of the subject invention are nucleic acids that have at least one ribose sugar at their 3' end with a free 3' hydroxyl group. The ribonucleic acids can be any desired chemically or/and enzymatically synthesized nucleic acid, e.g. a nucleic acid produced in vivo by a cell, which, apart from the 3'-terminal ribonucleotide, can contain any nucleotide units i.e. in particular deoxyribonucleotide or/and ribonucleotide units. However, nucleic acid acceptor molecules are preferred which have at least two and in particular at least three ribose sugars at their 3' end. Nucleic acid molecules are particularly preferred which are composed of more than 50% and essentially exclusively of ribonucleotide units i.e. ribonucleic acids, where ribonucleic acids of particular interest include either fragmented or unfragmented total RNA, polyA+RNA, and the like.

The ribonucleic acids are sufficiently long to be end-labeled according to the subject methods. Typically, the ribonucleic acids are at least 10 nt long, usually at least 20 nt long and more usually at least 30 nt long, where the ribonucleic acids may be significantly longer, e.g. the size of full length mRNA transcripts, etc.

By "end labeling" is meant that the non-radioactive label is stably attached, typically covalently bonded, to the 3' end of the ribonucleic acid, i.e. to the 3' terminal ribonucleotide of the ribonucleic acid. End-labeling according to the subject invention is accomplished by enzymatically attaching one or more, and in many cases a plurality of, non-radioactively labeled ribonucleotides to the 3' end of the ribonucleic acid, such that at least one and often a stretch or domain of sequentially attached non-radioactively labeled ribonucleotides are present at the 3' end of the end-labeled ribonucleic acid. By enzymatically attaching is meant that one or more non-radioactively labeled ribonucleotides are sequentially attached to the 3' terminal ribonucleotide of the ribonucleic acid with an enzyme having polymerase activity.

A critical feature of the subject invention is that the polymerase activity is provided by a prokaryotic polymerase, more specifically a bacterial polymerase, where the polymerase exhibits poly(A) polymerase activity. By poly(A) polymerase activity is meant that the polymerase adds ATP or analogues thereof to the 3' terminus of a ribonucleic acid, e.g. a polyribonucleotide, through a catalyzed polymerization reaction, where the resultant polyribonucleotide has at least one adenine base at its tail, and often has a poly(A) tail. Any convenient prokaryotic polymerase may be employed in the subject methods. A variety of bacterial poly(A) polymerases are known to those of skill in the art. Bacterial poly(A) polymerases of interest include poly(A) polymerases derived from: E. coli (e.g. E. coli PAP1 and E. coli PAP2); B. subtilis (e.g. B. subtilis PAP1 and B. subtilis PAP2); and the like. Suitable bacterial poly(A) polymerases can be purchased from a number of commercial sources, including: Life Technologies, Amersham Pharmacia Biotech, Sigma, and the like.

The non-radioactively labeled ribonucleotide employed in the subject methods is typically a modified adenine triphosphate, uracil triphosphate, cytosine triphosphate, guanosine triphosphate, (i.e. modified ATP or ATP analogue, modified UTP or UTP analogue; modified CTP or CTP analogue; modified GTP or GTP analogue) or a closely related analogue thereof, e.g. a deaza analogue thereof. The term analogue includes an ATP, UTP, CTP or GTP (or mimetic thereof) in which a moiety, typically the base, has been modified to be bonded to the non-radioactive label. In the non-radioactively labeled ribonucleotides, the heterocyclic nitrogenous base moiety, e.g. adenine analogue, uracil analogue, cytosine analogue or guanine analogue, is modified to provide a covalent attachment to the non-radioactive label, where the position of attachment of the ribonucleotide to the label is one that does not interfere with the ability of the ribonucleotide to serve as a substrate for the above described poly(A) polymerase and, preferably, does not interfere with the ability of the ribonucleotide to bond to subsequent ribonucleotides through phosphodiester linkages. In those embodiments where the labeled ribonucleotide is an ATP analogue, the label is typically bonded to the 7' position of the adenine moiety (i.e. the adenine analogue). In many embodiments, the adenine moiety or analogue is an alkynylamino-nucleotide as described in U.S. Pat. Nos. 5,047,519 and 5,151,507, the disclosures of which are herein incorporated by reference.

As mentioned above, the labeled ribonucleotide that is employed in the subject methods is a non-radioactively labeled ribonucleotide, specifically a non-radioactively labeled ribonucleotide analogue. Non-radioactive labels of interest are those that provide a detectable signal and do not substantially interfere with the ability of the labeled ribonucleotide to serve as a substrate for the poly(A) polymerase activity. Non-radioactive labels of interest include directly detectable and indirectly detectable labels. Directly detectable labels are those labels that provide a directly detectable signal without interaction with one or more additional chemical agents. Examples of directly detectable labels include fluorescent labels. Indirectly detectable labels are those labels which interact with one or more additional members to provide a detectable signal. In this latter embodiment, the label is a member of a signal producing system that includes two or more chemical agents that work together to provide the detectable signal. Examples of this latter embodiment include ligand for labeled antibodies, and the like. In many preferred embodiments, the label is a directly detectable label. Directly detectable labels of particular interest include fluorescent labels.

Fluorescent labels that find use in the subject invention include a fluorophore moiety. The fluorophores that find use in the subject methods are those that, when attached to a ribonucleotide, do not substantially inhibit enzymatic incorporation of the labeled ribonucleotide onto the 3' end of the ribonucleic acid. In many embodiments, the fluorescent moieties or fluorophores will have a size that ranges from about 200 to 2000 d, usually from about 200 to 1500 d, and more usually from about 300 to 1500 d. The excitation and emission maxima of the fluorescent dyes may vary substantially. Typically, fluorophores finding use in the subject invention will have an excitation maxima of from about 300 to 770, usually from about 310 to 770 and more usually from about 320 to 770 nm. The fluorophores will typically have an emission maxima of from about 300 to 800, usually from about 325 to 790 nm. For any given fluorescent dye, the difference between the emission and excitation maxima (i.e. Stokes shift) will typically be at least about 5 nm, where the difference may be as great as 200 nm or greater, but typically will not exceed about 35 nm. The extinction coefficient of the of the subject fluorophores generally exceeds at least about 10,000 $cm^{-1}$ $M^{-1}$ usually at least about 20,000 $cm^{-1}$ $M^{-1}$, and may be as high as 150,000 $cm^{-1}$ $M^{-1}$, or higher. The quantum yield will generally range from 0.1 to 1.0, more usually from 0.1 to 0.6.

The fluorophoric moieties or fluorophores of the fluorescently labeled ribonucleotides, may be cyclic, or polycyclic, particularly polycyclic, aromatic compounds having at least two rings, usually at least three rings and not more than six rings, more usually not more than five rings, where at least two of the rings are fused and in certain embodiments at least three of the rings are fused, where usually not more than four of the rings are fused. The aromatic compounds may be carbocyclic or heterocyclic, particularly having from one to three, more usually one to two nitrogen atoms as heteroannular atoms. Other heteroannular atoms may include oxygen and sulfur (chalcogen).

The rings may be substituted by a wide variety of substituents, which substituents may include alkyl groups of from one to six carbon atoms, usually from one to two carbon atoms, oxy, which includes hydroxy, alkoxy and carboxy ester, generally of from one to four carbon atoms, amino, including mono- and disubstituted amino, particularly mono- and dialkyl amino, of from 0 to 8, usually 0 to 6 carbon atoms, thio, particularly alkylthio from 1 to 4, usually 1 to 2 carbon atoms, sulfonate, including alkylsulfonate and sulfonic acid, cyano, non-oxo-carbonyl, such as carboxy and derivatives thereof, particularly carboxamide or carboxyalkyl, of from 1 to 8 or 1 to 6 carbon atoms, usually 2 to 6 carbon atoms and more usually 2 to 4 carbon atoms, oxo-carbonyl or acyl, generally from 1 to 4 carbon atoms, halo, particularly of atomic number 9 to 35, etc.

Specific fluorescent dyes of interest include: xanthene dyes, e.g. fluorescein and rhodamine dyes, such as fluorescein isothiocyanate (FITC), 6-carboxyfluorescein (commonly known by the abbreviations FAM and F),6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in microbiology applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc.

Of particular interest in many embodiments are xanthenic fluorophores or xanthenes, i.e. fluorophores having a xanthene moiety. In many embodiments, the xanthenic fluorophores will have a size that ranges from about 300 to 1200 d, usually from about 320 to 1100 d, and more usually from about 330 to 1000 d. The excitation and emission maxima of the xanthenic fluorophore may vary substantially. Typically, xanthenic fluorophores finding use in the subject invention will have an excitation maxima of from about 300 to 600, usually from about 310 to 600 and more usually from about 320 to 600 nm. The xanthenic fluorophores will typically have an emission maxima of from about 300 to 700, usually from about 325 to 675 nm. For any given xanthenic fluorophore, the difference between the emission and excitation maxima (i.e. Stokes shift) will typically range from about 15 to 70 nm, usually from about 15 to 30 nm. The extinction coefficient of the of the xanthenic fluorophores find use in the subject invention generally exceeds at least about 42,000 cm$^{-1}$ M$^{-1}$, usually at least about 50,000 cm$^{-1}$ M$^{-1}$, and may be as high as 130,000 cm$^{-1}$ M$^{-1}$, or higher. The quantum yield will generally range from 0.1 to 1.0, more usually from 0.1 to 0.6.

Xanthenic fluorophores of interest include those described by the following formula:

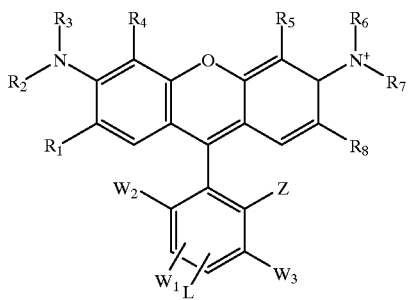

In the above formula, Z is an anionic group, preferably carboxylate or sulfonate, and more preferably carboxylate.

$R_1$ and $R_8$ taken alone are each hydrogen, halogen, alkyl (or substituted alkyl) having from 1 to 8 carbon atoms, alkylether (or substituted alkylether) having from 1 to 8 carbon atoms, or alkylthioether (or substituted alkylthioether) having from 1 to 8 carbon atoms, and $R_1$ taken together with $R_2$ and $R_8$ taken together with $R_7$ are alkyl chains each having from 2 to 5 carbon atoms connecting the 7' carbon to the nitrogen attached to the 6' carbon and connecting the 2' carbon to the nitrogen attached to the 3' carbon, respectively. $R_2$ and $R_7$ taken alone are each alkyl having from 1 to 8 carbon atoms, and $R_2$ taken together with $R_1$ and $R_7$ taken together with $R_8$ are each alkyl chains having from 2 to 5 carbon atoms as described above. $R_3$ and $R_6$ taken alone are each hydrogen or alkyl having from 1 to 8 carbon atoms, and $R_3$ taken together with $R_4$ and $R_6$ taken together with $R_5$ are alkyl chains each having from 2 to 5 carbon atoms connecting the 5' carbon to the nitrogen attached to the 6' carbon and connecting the 4' carbon to the nitrogen attached to the 3' carbon, respectively. $R_4$ and $R_5$ taken alone are hydrogen, alkyl having from 1 to 8 carbon atoms, halogen, alkylether having from 1 to 8 carbon atoms, or alkylthioether having from 1 to 8 carbon atoms, and $R_4$ taken together with $R_3$ and $R_5$ taken together with $R_6$ are alkyl chains each having from 2 to 5 carbon atoms as described above.

$W_1$, $W_2$, and $W_3$ are hydrogen or chloro, and preferably hydrogen.

L represents a linking group that serves as the covalent attachment to the ribonucleotide, i.e. the adenine analog moiety of the ribonucleotide. Exemplary linking groups include: —NH—CS—NH—; —C(O)NH—; and the like.

Xanthenic fluorophores of particular interest in many embodiments are: R6G, Lissamine, Fluoroscein and derivatives thereof, JOE, Tetremethyl rhodamine, ROX, and the like.

Of particular interest in other embodiments are polymethine compounds. Polymethine fluorophores of interest include cyanine compounds, merocyanine compounds and styryl compounds. See U.S. Pat. No. 5,268,486, the disclosure of which is herein incorporated by reference. Of particular interest are cyanine compounds. In many embodiments, the cyanine compounds or fluorophores will have a size that ranges from about 350 to 1200 d, usually from about 400 to 1000 d, and more usually from about 500 to 1000 d. The excitation and emission maxima of the cyanine fluorophores may vary substantially. Typically, fluorophores finding use in the subject invention will have an excitation maxima of from about 400 to 770 nm, usually from about 450 to 770 nm and more usually from about 500 to 770 run. The fluorophores will typically have an emission maxima of from about 460 to 800 nm, usually from about 460 to 790 run. For any given cyanine fluorophore, the difference between the emission and excitation maxima (i.e. Stokes shift) will range from about 10 to 30 nm, usually from about 10 to 25 nm and more usually from about 15 to 25 nm. The extinction coefficient of the of the subject cyanine fluorophores generally exceeds at least about 50,000 $cm^{-1} M^{-1}$ usually at least about 100,000 $cm^{-1} M^{-1}$, and may be as high as 150,000 $cm^{-1} M^{-1}$, or higher. The quantum yield will generally range from 0.1 to 1.0, more usually from 0.1 to 0.6.

Cyanine fluorophores of interest are generally described by the formula:

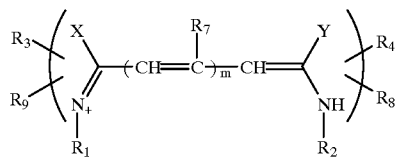

and are more specifically described by the following formulas:

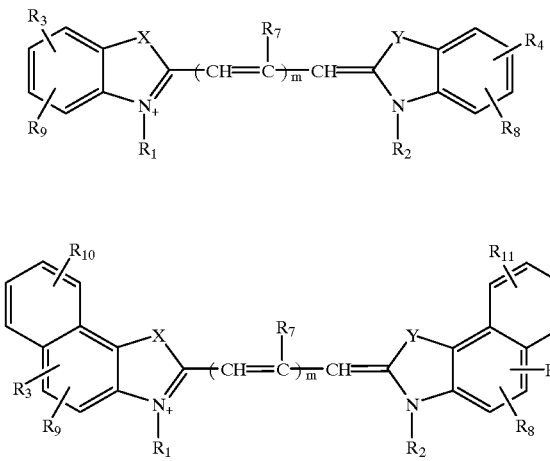

In the above formulas, X and Y are selected from the group consisting of O, S and isopropylidine (i.e. $—C(CH_3)_2—$). m is an integer selected from the group consisting of 1, 2, 3 and 4, where the number of methine groups determines in part the excitation color. At least one, preferably only one, and possibly two or more of said $R_1$, $R_2$, $R_3$, $R_4$, $R_5$, $R_6$ and $R_7$ groups in each molecule is a reactive group for attaching the fluorophore to the ribonucleotide. For certain reagents, at least one of said $R_1$, $R_2$, $R_3$, $R_4$, $R_5$, $R_6$, $R_7$ $R_8$, $R_9$, $R_{10}$ and, $R_{11}$ (if present) are independently H, cyano, alkyl, alkoxy, aryl, aryloxy, hydroxyl acyl, amino, cabonamido, or carbomoyl, reactive groups for attaching to functionalities present on ribonucleotides, or water solubility enhancing groups. Generally, $R_1$, $R_2$, $R_3$, $R_4$, $R_5$, $R_6$, $R_7$ $R_8$, $R_9$, $R_{10}$ and, $R_{11}$ are either H, reactive groups, water solubility enhancing groups or lower alkyls of 1 to 6 carbon atoms, usually 1 to 4 carbon atoms, where the alkyl may be straight chained or branched.

Reactive groups that may be attached directly or indirectly to the chromophore to form $R_1$, $R_2$, $R_3$, $R_4$, $R_5$, $R_6$, and $R_7$ groups may include reactive moieties such as groups containing isothiocyanate, isocyanate, monochlorotriazine, dichlorotriazine, mono- or di-halogen substituted pyridine, mono- or di-halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal and aldehyde.

In certain embodiments, the $R_1$, $R_2$, $R_3$, $R_4$, $R_5$, $R_6$ and $R_7$ groups can be selected from the well known polar and electrically charged chemical groups. Examples are —E—F, where F is hydroxy, sulfonate, sulfate, carboxylate, substituted amino or quaternary amino and where E is a spacer group such as $—(CH_2)_n$, where n is 0, 1, 2, 3 or 4. Useful examples include lower alkyls and alkyl sulfonate; $—(CH_2)_3—SO_3^{\oplus}$ and $—(CH_2)_4—SO_3^{\oplus}$. In the above formulas, at least one of said $R_8$, $R_9$ (if any) and $R_{10}$, $R_{11}$ (if any) groups comprises at least one sulfonate group. The term sulfonate is meant to include sulfonic acid, since the sulfonate group is ionized sulfonic acid.

The polymethine chain of cyanine fluorophores may also contain one or more cyclic chemical groups that form bridges between two or more of the carbon atoms of the polymethine chain.

Where cyanine fluorophores are employed to label the ribonucleotides of the subject invention, of particular interest are cyanine dyes of the following formula

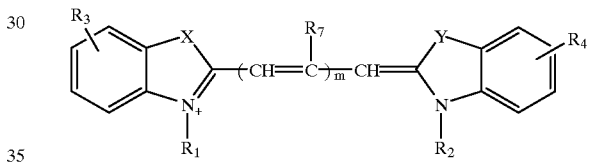

where X, Y, m, $R_1$, $R_2$, $R_3$, $R_4$ and $R_7$ are as described above. Of particular interest are Cy3 dyes, i.e. where m=1; Cy5 dyes, i.e. where m=2 and Cy7 dyes, where m=3, where Cy3 and Cy5 dyes are most preferred in many embodiments. In many embodiments, the dye is a Cy3 dye in which X and Y are each ($—C(CH_3)_2—$); $R_1$ is ethyl, $R_2$ is lower alkyl, e.g. from 1 to 3 carbon atoms, and $R_3$ and $R_4$ are each sulfonate/sulfonic acid.

Fluorophores suitable for use as in the fluorescently labeled ribonucleotides may be purchased commercially or readily synthesized, using procedures known in the literature.

Specific fluorophore labeled ribonucleotide analogues of interest include: UTP Analogs, e.g. Fluorescein-12-UTP, Coumarin-5-UTP, Tetramethylrhodamine-6-UTP, Texas Red-5-UTP, Lissamine-5-UTP, Naphthofluorescein-5-UTP, Fluorescein Chlorotriazinyl-4-UTP, Pyrene-8-UTP; CTP Analogs, e.g. Coumarin-5-CTP, Fluorescein-12-CTP, Tetramethylrhodamine-6-CTP,Texas Red-5-CTP, Lissamine-5-CTP, Naphthofluorescein-5-CTP, Fluorescein Chlorotriazinyl-4-CTP, Pyrene-8-CTP, Cyanine-3-CTP; ATP Analogs, e.g. Coumarin-5-ATP, Fluorescein-12-ATP, Tetramethylrhodamine-6-ATP, Texas Red-5-ATP, Lissamine-5-ATP; and the like.

The formulas for representative fluorescently labeled ribonucleotides of interest are provided below:

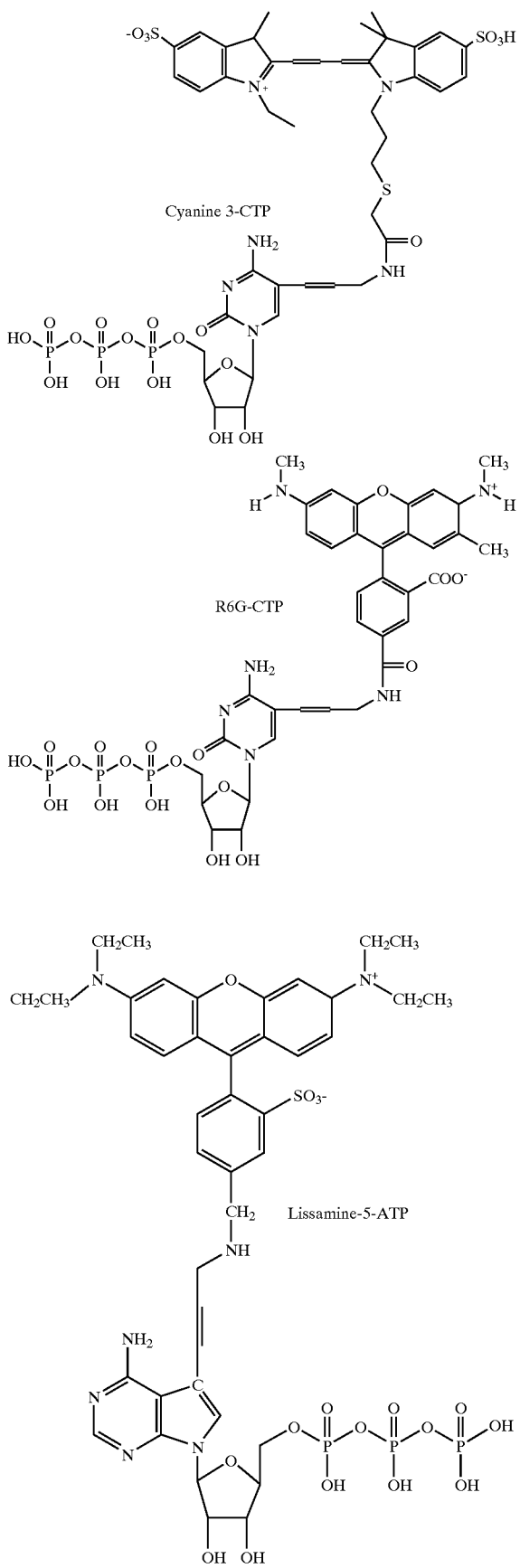
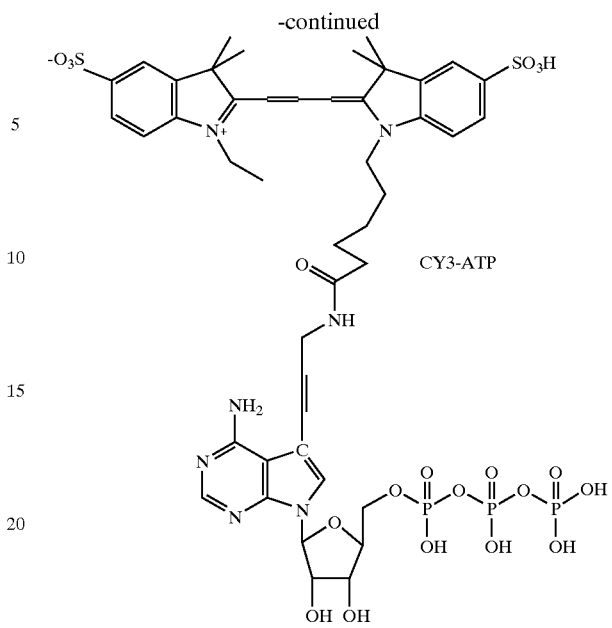

The above specific fluorescently labeled ribonucleotides, as well other non-radioactively labeled ribonucleotides, can be readily synthesized by those of skill in the art and/or purchased commercially.

In practicing the subject methods, the ribonucleic acid to be end-labeled is contacted with the labeled ribonucleotide in the presence of the prokaryotic poly(A) polymerase in a reaction mixture under conditions sufficient for at least one labeled ribonucleotide to be covalently bonded to the 3' terminal residue of the ribonucleic acid through a phosphodiester linkage. Typically, other reagents will be included in the reaction mixture that includes the ribonucleic acid, the labeled ribonucleotide and the poly(A) polymerase. Other reagents that are typically present include: buffering agents, e.g. Tris.HCl; cationic sources, both monovalent and divalent, e.g. NaCl, KCl, $MgCl_2$, $MnCl_2$; RNAase inhibitors; chelators, e.g. EDTA, and the like.

To accomplish the end-labeling reaction, the above agents are generally combined, either substantially simultaneously or even sequentially, into a reaction mixture and maintained at a suitable temperature for a sufficient period of time for the desired amount of terminal ribonucleotide incorporation to occur. The salt concentration in the reaction mixture typically ranges from about 50 to 500 mM, usually from about 50 to 250 mM and more usually is about 50 mM. In many embodiments, RNA concentrations typically range from about 1 femtomolar to 5 $\mu$M. The concentration of the labeled ribonucleotide typically ranges from about 100 $\mu$M. to 1 mM, usually from about 100 to 500 $\mu$M. The concentration of the prokaryotic poly(A) polymerase typically ranges from about 0.1 to 1.0 units per $\mu$l of reaction volume, where 1 unit equals the amount of enzyme needed to incorporate 1 nanomole of AMP into tRNA in 10 min at 37° C. Generally, the temperature of reaction mixture is held substantially constant at a value ranging from about 30 to 40, usually 35 to 40° C., where the temperature is typically about 37° C., and in many embodiments is 37° C. The time during which the reaction is allowed to proceed typically ranges from about 2 to 10 hours, usually from about 3 to 8 hours and more usually from about 3 to 6 hours. In many embodiments, sufficient end-labeling is accomplished in from about 3 to 5 hours, and often in from about 3.5 to 4.5 hours, e.g. 4 hours, where by sufficient is meant that at least 75%, usually at least 85% and more usually at least 95% and in many embodiments 99% or more, including 100%, of the ribonucleic acids have been modified at their 3' ends to include at least one labeled ribonucleotide.

The above steps of contacting the ribonucleic acid with the polymerase and labeled ribonucleotide result in the production of an end-labeled ribonucleic acid characterized by the presence of one or more labeled ribonucleotide residues sequentially attached to the 3' terminus of the original ribonucleic acid via a phosphodiester linkage. The number of labeled ribonucleotide analogue residues that may be attached is at least 1, may be at least 2, where the number may be as high as 5 or 10 or higher.

The conditions may be tailored to achieve a desired amount of labeled ribonucleotide incorporation. For example, where relatively low incorporation of label is desired, (e.g. 1 labeled ribonucleotide per molecule) shorter incubation times and/or smaller amounts of enzyme may be employed. Where relatively higher incorporate of label is desired, longer incubation times and/or larger amounts of enzyme may be employed.

Utility

The subject methods find use in applications where it is desired to end-label a ribonucleic acid with a non-radioactive, particularly a fluorescent, label. Such applications include: hybridization assays, in which the probe employed is an end-labeled ribonucleic acid of the subject invention, e.g. Southern analyses, northern analyses, DNA library screens, in situ hybridization experiments, e.g. chromosome squashes, tissue sections, etc.; sequencing applications, e.g. RNA direct chemical sequencing methods, as described in Weissman et al., supra; nucleic acid array/chip hybridizations, attachment to nucleic acid arrays, RNA binding assays, RNase protection assays and the like.

In hybridization assays according to the subject invention, an RNA sample suspected of comprising one or more RNAs of interest, i.e. target RNAs or RNA analytes, is end-labeled according to the subject end-labeling methods of the present invention. This presence or absence of the RNA target or analyte of interes in the sample is then determined by contacting the end-labeled RNA sample with a nucleic acid probe complementary to the RNA analyte. The probe may be present in a number of different media, e.g. on the surface of a solid support, as a member of an array of nucleic acid probes, e.g. on a nucleic acid array, etc. In hybridization assays according to the subject invention, the end labeled sample suspected of comprising the target ribonucleic acid (i.e. analyte) is contacted with the nucleic acid probe under conditions sufficient for the labeled target RNA, if present, to bind to the probe nucleic acid. Thus, if the analyte of interest is present in the sample being assayed, a complex is formed between the labeled ribonucleic acid and the probe nucleic acid. The presence of this binding complex is then detected via the fluorescent label. The presence of the target in the sample being interrogated is then deduced from the detection of binding complexes.

Specific hybridization assays of interest include those in which the probe nucleic acid is present on the surface of a nucleic acid array. In these assays, a sample of target nucleic acids (i.e. end labeled ribonucleic acids, where the ribonucleic acids are prepared according to the subject methods) is first prepared. Following sample preparation, the sample is contacted with the array under hybridization conditions, whereby complexes are formed between target nucleic acids that are complementary to probe sequences attached to the array surface. The presence of hybridized complexes is then detected. Specific examples of such hybridization assays include: gene discovery assays, differential gene expression analysis assays; nucleic acid sequencing assays; polymorphism detection assays; genotyping assays; and the like.

Kits

Also provided are kits for use in practicing the methods of the subject invention. The subject kits typically include at least a prokaryotic poly(A) polymerase, as described supra, and a non-radioactively labeled ribonucleotide, e.g. fluorescently labeled ATP, fluorescently labeled CTP, fluorescently labeled UTP, fluorescently labeled GTP, and the like. The subject kits may further include additional reagents necessary and/or desirable for use in practicing the subject methods, where additional reagents of interest include: an aqueous buffer medium (either prepared or present in its constituent components, where one or more of the components may be premixed or all of the components may be separate); RNase inhibitors, control substrates, control RNAs, and the like. The various reagent components of the kits may be present in separated containers, or may all be pre-combined into a reagent mixture for combination with to be labeled ribonucleic acid. A set of instructions will also typically be included, where the instructions may associated with a package insert and/or the packaging of the kit or the components thereof.

The following examples are offered by way of illustration and not by way of limitation.

EXPERIMENTAL

To label 40 picomoles of RNA with the fluorescent nucleotide cyanine-3 ATP (Cy3-ATP) (see structure, supra), the following components are mixed together in a volume of 20 µl:

1. 40 pmols RNA
2. 100 mM NaCl
3. 20 mM Tris-HCl (pH 7.0)
4. 3.35 mM $MnCl_2$
5. 0.2 mM EDTA
6. 10% glycerol
7. 100 µg/ml bovine serum albumin
8. 0.1 mM Cy3-ATP
9. 5 units placental ribonuclease inhibitor (Life Technologies)
10. 9.6 units *E. coli* poly(A) polymerase (Life Technologies)

The reaction is incubated at 37° C. for four fours. For RNAs longer than 30 nt, approximately one Cy3-ATP is added per RNA as measure spectrophotometrically. RNAs smaller than 30 bases in length are not efficiently labeled, with only about 20% incorporation seen with an RNA of 19 bases.

In a second experiment, 1.2 femtomoles of RNA were labeled using the above described conditions, except that the total volume of the reaction was 10 µl and the amounts of Cy3-ATP and poly(A) polymerase were reduced by half. Under these reaction conditions, approximately 10–12 Cy3-ATPs were added to each RNA, as determined by gel electrophoresis.

The above methods provide a number of advantages over those methods described in the Background section, supra. First, the subject invention provides a method for attaching fluorescently labeled ribonucleotides to the 3' ends of RNAs using a prokaryotic poly(A) polymerase. Second, the subject invention provides a method for specifically end-labeling RNAs to the exclusion of DNAs, even in situations where DNAs are present. Furthermore, the invention uses commercially available reagents, such as bacterial poly(A) polymerases and fluorescently labeled ribonucleotides. The reaction conditions employed in the subject methods are not harsh, and no chemical reactions are employed which could substantially degrade the RNA. In addition, the subject methods are relatively quick, taking on average about four hours. Labeling according to the subject methods is relatively efficient, and multiple labels can be added per RNA molecule provided the appropriate conditions are employed. As such, the subject methods represent a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A kit for use in end-labeling ribonucleic acids with non-radioactively labeled ribonucleotides, said kit comprising:

a fluorescently labeled ribonucleotide; and a bacterial poly(A) polymerase.

2. The kit according to claim 1, wherein said fluorescently labled ribonucleotide is a fluorescently labeled ATP analog, CTP analog, UTP analog or GTP analog.

3. The kit according to claim 1, wherein said fluorescently labeled ribonucleotide contains a modified nitrogenous base moiety covalently bonded to a fluorescent label.

4. The kit according to claim 1, wherein said fluorescently labeled ribonucleotide is labeled with a xanthenic fluorophore or polymethine fluorophore.

5. The kit according to claim 4, wherein said polymethine fluorophore is a cyanine fluorophore.

6. The kit according to claim 1, wherein said fluorescently labeled ribonucleotide is labeled with a fluorophore chosen from Pyrene, Coumarin, Diethylaminocoumarin, PAM, Fluorescein Chlorotriazinyl, Fluorescein, R110, Easin, JOE, R6G, Tetramethyirhodamine, TAMRA, Lissamine, ROX, Napthofiuorescein, Texas Red, FITC, HEX, Cy3, Cy5 and Cy7.

7. The kit according to claim 1, wherein said bacterial polymerase is chosen from Escherichia coli poly(A) polymerase 1, Escherichia coli poly(A) polymerase 2, Bacillus subtilis poly(A) polymerase 1, and Bacillus subtilis poly(A) polymerase 2.

8. A kit for use in end-labeling ribonucleic acids with non-radioactively labeled ribonucleotides, said kit comprising:

a fluorescently labeled ribonucleotide labeled with a xanthenic fluorophore or cyanine fluorophore; and a prokaryotic poly (A) polymerase.

9. The kit according to claim 8, wherein said fluorescently labeled ribonucleotide is an ATP analog, CTP analog, UTP analog or GTP analog labeled with a Xanthenic fluorophore or Cyanine fluorophore.

10. The kit according to claim 8, wherein said fluorescently labeled ribonucleotide contains a modified nitrogenous base moiety covalently bonded to said fluorophore.

11. The kit according to claim 8, wherein said fluorescently labeled ribonucleotide is labeled with a Xanthenic fluorophore chosen from FAM, Fluorescein Chlorotriazinyl, Fluorescein, JOE, R110, R6G, Tetramethylrhodaniine, TAMRA, Lissaniine, ROX, FITC, and HEX.

12. The kit according to claim 8, wherein said fluorescently labeled ribonucleotide is labeled with a cyanine fluorophore chosen from Cy3, Cy5 and Cy7.

13. The kit according to claim 8, wherein said prokaryotic poly(A) polymerase is a bacterial polymerase.

14. The kit according to claim 13, wherein said bacterial polymerase is chosen from Escherichia coli poly(A) polymerase 1, Escherichia coli poly(A) polymerase 2, Bacillus subtilis poly(A) polymerase 1, and Bacillus subtilis poly(A) polymerase 2.

* * * * *